United States Patent [19]

Flick et al.

[11] Patent Number: 5,801,267
[45] Date of Patent: Sep. 1, 1998

[54] PREPARATION OF ALIPHATIC ALPHA, OMEGA-AMINONITRILES

[75] Inventors: Klemens Flick, Herxheim; Johann-Peter Melder, Mannheim; Werner Schnurr, Herxheim; Klaus Ebel, Lampertheim; Tom Witzel, Ludwigshafen; Wolfgang Harder, Weinheim; Alwin Rehfinger, Mutterstadt; Rolf Fischer, Heidelberg, all of Germany

[73] Assignee: BASF Aktiengesellschaft, Ludwigshafen, Germany

[21] Appl. No.: 846,239

[22] Filed: Apr. 28, 1997

Related U.S. Application Data

[60] Division of Ser. No. 648,702, May 16, 1996, which is a continuation-in-part of Ser. No. 375,573, Jan. 18, 1995, Pat. No. 5,527,946.

[30] Foreign Application Priority Data

Dec. 27, 1994 [DE] Germany .................. 44 46 893.8

[51] Int. Cl.$^6$ .................. C07C 255/03; C07C 255/24
[52] U.S. Cl. .................. 558/459; 558/452
[58] Field of Search .................. 558/452, 459

[56] References Cited

U.S. PATENT DOCUMENTS

| | | | |
|---|---|---|---|
| 4,389,348 | 6/1983 | Diamond et al. | 260/465.5 R |
| 4,601,859 | 7/1986 | Galle et al. | 558/459 |

OTHER PUBLICATIONS

Stiles, Alvin, *Catalyst Manufacture*, 1983, pp. 123–124.
Sittig, Marshall, *Catalyst Manufacture*, 1972, pp. 217–221.
*Ullmann's Enc. of Ind. Chem.*, 5th Edition, vol. A2, 1979, pp. 169–172.
Leach, Bruce E., *Applied Industrial Catalysis*, vol. 2, 1983, pp. 177–180.

Primary Examiner—Joseph McKane
Assistant Examiner—Jane C. Osweck
Attorney, Agent, or Firm—Keil & Weinkauf

[57] ABSTRACT

Aliphatic alpha,omega-aminonitriles are prepared by partial hydrogenation of aliphatic alpha,omega-dinitriles at elevated temperatures and superatmospheric pressure in the presence of a solvent and of a catalyst by a process in which the catalyst (a) contains a compound based on a metal selected from the group consisting of nickel, cobalt, iron, ruthenium and rhodium and (b) contains from 0.01 to 25% by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals and (c) from 0 to 5% by weight, based on (a), of a compound based on an alkali metal or on an alkaline earth metal, with the proviso that the component (a) is not based on iron or iron and one of the metals selected from the group consisting of cobalt, ruthenium and rhodium when (b) is a promoter based on a metal selected from the group consisting of titanium, manganese, chromium and molybdenum, and with the further proviso that, when a compound based on only ruthenium or ruthenium and rhodium or nickel and rhodium is selected as component (a), the promoter (b) may be dispensed with.

1 Claim, No Drawings

PREPARATION OF ALIPHATIC ALPHA, OMEGA-AMINONITRILES

This is a divisional of application Ser. No. 08/648,702, filed May 16, 1996 now allowed which is a C-I-P of Ser. No. 08/375,573, filed Jan. 18, 1995, now U.S. Pat. No. 5,527, 946.

The present invention relates to an improved process for the preparation of aliphatic alpha,omega-aminonitriles by partial hydrogenation of aliphatic alpha,omega-dinitriles at elevated temperature and superatmospheric pressure in the presence of a solvent and a catalyst.

WO 92/21650 describes the partial hydrogenation of adiponitrile to 6-aminocapronitrile in the presence of a Raney nickel catalyst and ammonia as a solvent in a yield of 60% at a conversion of 70%. is formed in the amount of 9% as a byproduct. The disadvantage of this process is the short life of the catalyst.

U.S. Pat. No. 2,257,814 and U.S. Pat. No. 2,208,598 likewise describe preparation processes of 6-aminocapronitrile starting from adiponitrile, the catalysts used being Raney cobalt or iron, nickel and cobalt catalysts on various carriers. The fact that the selectivities of from 50 to 60% are too low for industrial applications is a disadvantage of these processes.

In the process of WO 93/16034, the yield of aminocapronitrile can be increased by hydrogenating adiponitrile in the presence of Raney nickel, of a base, such as sodium hydroxide, potassium hydroxide, lithium hydroxide or ammonium hydroxide, and of a transition metal complex containing, for example, iron, cobalt, chromium or tungsten as transition metals, and of a solvent. In this process, quantitative yields of aminocapronitrile are said to be obtained at conversions of from 45 to 60%. The disadvantage of this process is the working up of the generally toxic transition metal complexes from the reaction mixtures obtained.

EP-A 161,419 describes the partial hydrogenation of adiponitrile using a rhodium-containing catalyst on a magnesium oxide carrier. At a conversion of 70%, a selectivity of 94% is achieved. The disadvantage is the expensive preparation method of the Rh/MgO catalysts (cf. J. of Cat. 112 (1988), 145–156).

DE-A 4,235,466 describes the fixed-bed hydrogenation of adiponitrile to 6-aminocapronitrile over an iron sponge catalyst (unsupported catalyst) which was prepared from iron ore by a special method and subsequently doped with cobalt, titanium, manganese, chromium, molybdenum, ruthenium or iridium. Owing to the small surface area (0.8 m²/g), these catalysts generally have useful activity only at high pressures and high temperatures. A further disadvantage of this process is the rapid loss of activity: in spite of a reduction in the adiponitrile and hydrogen loading, which leads to an increase in conversion, according to Example 7 the conversion decreased by 5% in the course of 24 hours.

DE-A 848,654 describes the continuous fixed-bed hydrogenation of adiponitrile over palladium on silica gel and over metals of the eighth group of the Periodic Table, these metals preferably being used in the form of spinels. A substantial disadvantage of these catalysts is their unsatisfactory life.

It was found that catalysts based on iron with a BET-surface (Bruna Ver-Emmett-Teller) of greater than 5 m²/g and a carbon content of not more than 0.4% by weight, based on the total amount of the catalyst, are very useful for the preparation of aliphatic alpha,omega-aminonitriles by partial hydrogenation of aliphatic alpha,omega-dinitriles. Such Fe-catalysts are known and used as catalysts in the synthesis of ammonia, the Fisher-Tropsch-reaction or the preparation of styrene from ethyl benzene. The corresponding iron oxide precursors are obtainable from iron oxides such as hematite or magnetite or by oxidation of iron or starting from iron cyanides, carbides, and nitrides according to Ullmann's Encyclopedia of Industrial Chemistry, 5th Edition, vol. A2, p. 169–172. Promotors may be added by melting the corresponding oxides or by well-known impregnation techniques. Iron oxide precursors are also obtainable by precipitation methods (for-example described in B. E. Leach, Applied Industrial Catalysis, vol. 2, 1983, pp. 177–180) or by co-precipitation on inert oxidic carriers by adding starting from aqueous solutions of iron salts and with carbonates or hydroxides. The obtained precursors can be transformed into extrudates or pellets as described for example in Catalyst Manufacture, A. B. Stiles (1983), pp. 123–124 and M. Sittig, Catalyst Manufacture, Recovery and Use, 1972, Noyes data corporation, pp. 217–221.

It is an object of the present invention to provide an improved process for the preparation of aliphatic alpha, omega-aminonitriles by partial hydrogenation of adiponitrile, which process does not have the abovementioned disadvantages; in particular, it is intended to provide a process in which the catalysts used have a longer life than those of the prior art.

We have found that this object is achieved by a process for the preparation of aliphatic alpha,omega-aminonitriles by partial hydrogenation of aliphatic alpha,omega-dinitriles at elevated temperatures and superatmospheric pressure in the presence of a solvent and of a catalyst, which comprises using a catalyst which (a) contains a compound based on a metal selected from the group consisting of nickel, cobalt, iron, ruthenium or rhodium and (b) contains from 0.01 to 25, preferably from 0.1 to 5, % by weight, based on (a), of a promoter based on a metal selected from the group consisting of palladium, platinum, iridium, osmium, iron, copper, silver, gold, chromium, molybdenum, tungsten, manganese, rhenium, zinc, cadmium, lead, aluminum, tin, phosphorus, arsenic, antimony, bismuth or rare earth metals and (c) from 0 to 5% by weight, based on (a), of a trace component based on a metal selected from the group consisting of an alkali metal and an alkaline earth metal, with the proviso that the component (a) is not based on iron or iron and one of the metals selected from the group consisting of cobalt, ruthenium and rhodium when (b) is a promoter based on a metal selected from the group consisting of titanium, manganese, chromium and molybdenum, and with the further proviso that, when a compound based on only ruthenium or rhodium or ruthenium and rhodium or rhodium and nickel is selected as component (a), the promoter (b) may, if desired, be dispensed with, whereby the catalyst is obtained by (I) impregnating a catalyst carrier with a solution of the components (a), (b) and, if desired, (c), where the individual components may be added simultaneously or in succession, or by spraying the solutions of the components (a), (b) and, if desired, (c) onto the carrier by a method known per se, then (II) if desired processing the resulting impregnated carrier to give extrudates or pellets, then (III) drying the impregnated carrier, extrudates or pellets at a temperature from 80° to 150° C. yielding a dried product, and (IV) then calcining the dried product at a temperature from 150° to 1000° C. in a gas stream comprising air or nitrogen yielding a calcined product, then (V) if desired, passivating the surface of the calcined product at from 20° to 80° C. by means of an oxygen/nitrogen mixture yielding a passivated product, then (VI) activating the calcined or passivated product by exposing it to a reducing atmosphere for from 2 to 24 hours at from 200° to 500° C.

In another embodiment of the invention, the objective stated above can be achieved by a process for the preparation of aliphatic alpha,omega-aminonitriles by partial hydrogenation of aliphatic alpha,omega-dinitriles at elevated temperature and superatmospheric pressure in the presence of a solvent and of a catalyst, which comprises carrying out the partial dehydrogenation in the presence of a catalyst which (a) contains a compound based on a metal selected from the group consisting of iron, nickel, ruthenium and rhodium and (b) contains from 0.01 to 25% by weight, based on (a), of a promoter based on a metal selected from the group consisting of palladium, platinum, iridium, osmium, iron, copper, silver, gold, chromium, molybdenum, tungsten, manganese, rhenium, zinc, cadmium, lead, aluminum, tin, phosphorus, arsenic, antimony, bismuth and rare earth metals, and (c) from 0 to 5% by weight, based on (a), of a trace component based on a metal selected from the group consisting of an alkali metal and an alkaline earth metal, with the proviso that the component (a) is not based on iron or iron and one of the metals selected from the group consisting of cobalt, ruthenium and rhodium when (b) is a promoter based on a metal selected from the group consisting of titanium, manganese, chromium and molybdenum, and with the further proviso that, when a compound based on only ruthenium or rhodium or ruthenium and rhodium or rhodium and nickel is selected as component (a), the promoter (b) may, if desired, be dispensed with, whereby the catalyst is obtained by (I) precipitating precursors of the components (a) to (c) from aqueous solutions in the presence or absence of carriers yielding a precipitate, then (II) if desired processing the resulting precipitate to give extrudates or pellets, then (III) drying the precipitate or pellets or extrudates at a temperature from 80° to 150° C. yielding a dried product, and (IV) then calcining the dried product at a temperature from 150° to 1000° C. in a gas stream comprising air or nitrogen yielding a calcined product, then (V) if desired, passivating the surface of the calcined product at from 20° to 80° C. by means of an oxygen/nitrogen mixture yielding a passivated product, then (VI) activating the calcined or passivated product by exposing it to a reducing atmosphere for from 2 to 24 hours at from 200° to 500° C.

In yet another embodiment of the invention, the objective stated above can be achieved by a process for the preparation of aliphatic alpha,omega-aminonitriles by partial hydrogenation of aliphatic alpha,omega-dinitriles at elevated temperature and superatmospheric pressure in the presence of a solvent and of a catalyst, which comprises using a catalyst which (a) contains iron and (b) contains from 0.01 to 25% by weight, based on (a), of a promoter based on a metal selected from the group consisting of palladium, platinum, iridium, osmium, iron, copper, silver, gold, tungsten, rhenium, zinc, cadmium, lead, aluminum, tin, phosphorus, arsenic, antimony, bismuth and rare earth metals, and (c) from 0 to 5% by weight, based on (a), of a trace component based on a metal selected from the group consisting of an alkali metal and an alkaline earth metal, whereby the catalyst has a BET-surface of not smaller than 5 $m^2/g$ and a carbon content of not greater than 0.4% by weight, based on the total amount of catalyst.

Preferred catalysts are those in which the component (a) contains at least one compound based on a metal selected from the group consisting of nickel, cobalt and iron, in an amount of from 10 to 95% by weight, and ruthenium and/or rhodium in an amount of from 0.1 to 5% by weight, based in each case on the sum of the components (a) to (c), the component (b) contains at least one promoter based on a metal selected from the group consisting of silver, copper, manganese, rhenium, lead and phosphorus, in an amount of from 0.1 to 5% by weight, based on (a), and the component (c) contains at least one compound based on the alkali metals and alkaline earth metals selected from the group consisting of lithium, sodium, potassium, cesium, magnesium and calcium, in an amount of from 0.1 to 5% by weight.

Particularly preferred catalysts are:

catalyst A, containing 90% by weight of cobalt oxide (CoO), 5% by weight of manganese oxide ($Mn_2O_3$), 3% by weight of phosphorus pentoxide and 2% by weight of sodium oxide ($Na_2O$), catalyst B, containing 20% by weight of cobalt oxide (CoO), 5% by weight of manganese oxide ($Mn_2O_3$), 0.3% by weight of silver oxide ($Ag_2O$), 70% by weight of silica ($SiO_2$), 3.5% by weight of alumina ($Al_2O_3$), 0.5% by weight of iron oxide ($Fe_2O_3$), 0.5% by weight of magnesium oxide (MgO) and 0.5% by weight of calcium oxide (CaO), and catalyst C, containing 20% by weight of nickel oxide (NiO), 66.4% by weight of silica ($SiO_2$), 3.7% by weight of alumina ($Al_2O_3$), 0.8% by weight of iron oxide ($Fe_2O_3$), 0.76% by weight of magnesium oxide (MgO), 1.92% by weight of calcium oxide (CaO), 3.4% by weight of sodium oxide ($Na_2O$) and 2.0% by weight of potassium oxide ($K_2O$).

The catalysts which can be used according to the invention may be unsupported or supported catalysts. Examples of suitable carriers are porous oxides, such as alumina, silica, aluminosilicates, lanthanum oxide, titanium dioxide, zirconium dioxide, magnesium oxide, zinc oxide and zeolites, as well as active carbon or mixtures thereof.

As a rule, the preparation is carried out by precipitating precursors of the component (a) together with precursors of the promoters (components (b) and, if desired, with precursors of the trace components (c) in the presence or absence of carriers (depending on which catalyst type is desired), if desired processing the resulting catalyst precursor to give extrudates or pellets, drying the latter and then calcining them. Supported catalysts are also obtainable in general by impregnating the carrier with a solution of the components (a), (b) and, if desired, (c), where the individual components may be added simultaneously or in succession, or by spraying the components (a), (b) and, if desired, (c) onto the carrier by a method known per se.

Suitable precursors of the components (a) are as a rule readily water-soluble salts of the abovementioned metals, such as nitrates, chlorides, acetates, formates and sulfates, preferably nitrates.

Suitable precursors of the components (b) are as a rule readily water-soluble salts or complex salts of the abovementioned metals, such as nitrates, chlorides, acetates, formates and sulfates and in particular hexachloroplatinate, preferably nitrates and hexachloroplatinate.

Suitable precursors of the components (c) are as a rule readily water-soluble salts of the abovementioned alkali metals and alkaline earth metals, such as hydroxides, carbonates, nitrates, chlorides, acetates, formates and sulfates, preferably hydroxides and carbonates.

The precipitation is carried out in general from aqueous solutions, either by adding precipitating reagents or by changing the pH or the temperature.

The preliminary catalyst material thus obtained is usually dried, in general at from 80° to 150° C., preferably from 80° to 120° C.

Calcining is usually carried out at from 150° to 1000° C., preferably from 200° to 450° C., in a gas stream comprising air or nitrogen.

After the calcination, the catalyst material obtained is generally exposed to a reducing atmosphere (activation), for example to a hydrogen atmosphere or a gas mixture containing hydrogen and an inert gas, such as nitrogen, for from 2 to 24 hours at from 80° to 250° C., preferably from 80° to 180° C., in the case of catalysts based on ruthenium or rhodium as component (a) or from 200° to 500° C., preferably from 250° to 400° C., in the case of catalysts based on a metal selected from the group consisting of nickel, cobalt and iron as component (a). The catalyst space velocity here is preferably 200 liter per liter of catalyst.

The activation of the catalyst is advantageously carried out directly in the synthesis reactor, since this usually dispenses with an otherwise necessary intermediate step, ie. the passivation of the surface at, usually, from 20° to 80° C., preferably from 25° to 35° C., by means of an oxygen/nitrogen mixture, such as air. The activation of passivated catalysts is then preferably effected in the synthesis reactor at from 180° to 500° C., preferably from 200° to 350° C., in a hydrogen-containing atmosphere.

The catalysts may be used as fixed-bed catalysts by the liquid-phase or trickle-bed procedure or as suspension catalysts.

The starting materials used in the novel process are aliphatic alpha,omega-dinitriles of the general formula I

   I where n is an integer from 1 to 10, in particular 2, 3, 4, 5 or 6. Particularly preferred compounds I are succinonitrile, glutaronitrile, adiponitrile, pimelonitrile and suberonitrile, very particularly preferably adiponitrile.

In the novel process, the dinitriles I described above are partially hydrogenated in the presence of a solvent using a catalyst to give alpha,omega-aminonitriles of the general formula II

   II where n has the abovementioned meanings. Particularly preferred aminonitriles II are those in which n is 2, 3, 4, 5 or 6, in particular 4, ie. 4-aminobutyronitrile, 5-aminopentanenitrile, 6-aminohexanenitrile (6-aminocapronitrile), 7-aminoheptanenitrile and 8-aminooctanenitrile, very particularly preferably 6-aminocapronitrile.

If the reaction is carried out in a suspension, temperatures of from 40° to 150° C., preferably from 50° to 100° C., particularly preferably from 60° to 90° C., are usually chosen; the pressure is chosen in general to be from 2 to 20, preferably from 3 to 10, particularly preferably from 4 to 9, MPa. The residence times are essentially dependent on the desired yield and selectivity and on the desired conversion; usually, the residence time is chosen so that a maximum yield is obtained, for example from 50 to 275, preferably from 70 to 200, minutes when adiponitrile is used.

In the suspension procedure, preferably used solvents are ammonia, amines, diamines and triamines of 1 to 6 carbon atoms, such as trimethylamine, triethylamine, tripropylamine and tributylamine, or alcohols, in particular methanol and ethanol, particularly preferably ammonia. A dinitrile concentration of from 10 to 90, preferably from 30 to 80, particularly preferably from 40 to 70, % by weight, based on the sum of dinitrile and solvent, is advantageously chosen.

The amount of catalyst is chosen in general so that the amount of catalyst is from 1 to 50, preferably from 5 to 20, % by weight, based on the amount of dinitrile used.

The suspension hydrogenation can be carried out batchwise or, preferably, continuously, as a rule in the liquid phase.

The partial hydrogenation can also be carried out batchwise or continuously in a fixed-bed reactor by the trickle-bed or liquid-phase procedure, a temperature of from 20° to 150° C., preferably from 30° to 90° C., and a pressure of, as a rule, from 2 to 30, preferably from 3 to 20, MPa generally-being chosen. According to the invention, the partial hydrogenation is carried out in the presence of a solvent, preferably ammonia, amines, diamines and triamines of 1 to 6 carbon atoms, such as trimethylamine, triethylamine, propylamine and tributylamine, or alcohols, preferably methanol and ethanol, particularly preferably ammonia. In a preferred embodiment, an ammonia content of from 1 to 10, preferably from 2 to 6, g per g of adiponitrile is chosen. A catalyst space velocity of from 0.1 to 2.0, preferably from 0.3 to 1.0, kg of adiponitrile per 1 per h is chosen. The conversion and hence the selectivity can be controlled by changing the residence time in this case too.

In the novel process, alpha,omega-aminonitriles are obtained in good selectivities and with only small amounts of hexamethylenediamine. Furthermore, the catalysts used according to the invention have a substantially longer life than comparable prior art catalysts. The alpha,omega-aminonitriles are important starting compounds for the preparation of cyclic lactams, in particular 6-aminocapronitrile for caprolactam.

EXAMPLES

Comparative Example 1: (Example 2 in DE-A 848, 654)

A tube reactor having a length of 4.5 m and an internal diameter of 0.6 cm was filled with 105 ml (96 g) of catalyst consisting of 2.3% by weight of PdO on $SiO_2$ (remainder), and the catalyst was then activated at atmospheric pressure in the course of 48 hours in a stream of hydrogen (200 l/h) by increasing the temperature from 30° C. to 250° C. After the temperature had been reduced to 120° C., a mixture of 55 ml/h of adiponitrile (ADN), 130 ml/h of ammonia and 200 l/h of hydrogen was fed to the reactor at 180 bar. Under these conditions, 13% of the adiponitrile were converted. The reaction mixture consisted essentially of 87% by weight of ADN and 3.3% by weight of ACN ($^6$-aminocapronitrile). Under these conditions, the catalyst lost 3% of its initial activity per hour of operation.

Comparative Example 2: (Example 4 in DE-A 848, 654)

Using 4% by weight of CuO, 4% by weight of ZnO and 16.6% by weight of $Co_2O_3$ on $SiO_2$ (remainder) as the catalyst, a mixture of 55 ml/h of adiponitrile, 130 ml/h of ammonia and 200 l/h of hydrogen was reacted to a conversion of 50% at 80° C. and 180 bar in the same reactor as in Comparative Example 1. The reacted mixture consisted of 50% by weight of ADN, 40% by weight of ACN and 9% by weight of HMD (hexamethylenediamine). By increasing the reaction temperature to 95° C., the conversion increased to 69%. The reaction mixture consisted essentially of 31% by weight of ADN, 46% by weight of ACN and 21% by weight of HMD. Under these conditions, the catalyst lost 1% of its initial activity per hour of operation, and the moldings had completely disintegrated after 60 hours.

Comparative Example 3: (Example 3 in DE-A 848, 654)

Using 7.5% by weight of CoO and 16% by weight of $Fe_2O_3$ on $SiO_2$ (remainder) as a catalyst, a mixture of 55 ml/h of adiponitrile, 130 ml/h of ammonia and 200 l/h of hydrogen was reacted to a conversion of 45% at 70° C. and 180 bar in the same reactor as in Comparative Example 1. The reacted mixture consisted essentially of 55% by weight of ADN, 37% by weight of ACN and 7% by weight of HMD. By increasing the reaction temperature to 85° C., the conversion increased to 78%. The reaction mixture consisted essentially of 22% by weight of ADN, 48% by weight of ACN and 27% by weight of HMD. The catalyst lost 0.5% of its initial activity per hour of operation, and 10% of its initial activity in the course of 24 hours.

Example 1

A tube reactor having a length of 2 m and an internal diameter of 2.5 cm was filled with 750 ml (1534 g) of catalyst consisting of 90% by weight of CoO, 5% by weight of $Mn_2O_3$, 3% by weight of $P_2O_5$ and 2% by weight of $Na_2O$, and the catalyst was then activated at atmospheric pressure in the course of 48 hours in a stream of hydrogen (500 l/h) by increasing the temperature from 30° C. to 280° C. After the temperature had been decreased to 60° C., a mixture of 400 ml/h of adiponitrile, 930 ml/h of ammonia and 500 l/h of hydrogen was fed to the reactor at 200 bar. Under these conditions, 46% of adiponitrile were converted. The reaction mixture consisted essentially of 54% by weight of ADN, 37% by weight of ACN and 9% by weight of HMD. By increasing the reaction temperature to 70° C., the conversion increased to 65%. The reaction mixture consisted essentially of 34.5% by weight of ADN, 46% by weight of ACN and 19.5% by weight of HMD. After 900 hours, the catalyst still had the same selectivity as fresh catalyst, the activity being unchanged. The catalyst moldings were still intact after removal (after 900 hours).

Example 2

A tube reactor having a length of 4.5 m and an internal diameter of 0.6 cm was filled with 105 ml (96 g) of catalyst consisting of 20% by weight of CoO, 5% by weight of $Mn_2O_3$, 0.3% by weight of $Ag_2O$, 70% by weight of $SiO_2$, 3.5% by weight of $Al_2O_3$, 0.4% by weight of $Fe_2O_3$, 0.4% by weight of MgO and 0.4% by weight of CaO, and the catalyst was then activated at atmospheric pressure in the course of 48 hours in a stream of hydrogen (200 l/h) by increasing the temperature from 30° C. to 250° C. After the temperature had been decreased to 90° C., a mixture of 55 ml/h of adiponitrile, 130 ml/h of ammonia and 200 l/h of hydrogen was fed to the reactor at 180 bar. Under these conditions, 30% of the adiponitrile were converted. The reaction mixture consisted essentially of 65% by weight of ADN, 30% by weight of ACN and 4% by weight of HMD. By increasing the reaction temperature to 100° C., the conversion increased to 71%. The reaction mixture consisted essentially of 29% by weight of ADN, 53% by weight of ACN and 18% by weight of HMD. After 300 hours, the catalyst still had the same selectivity as fresh catalyst, the activity being unchanged.

Example 3

A tube reactor having a length of 4.5 m and an internal diameter of 0.6 cm was filled with 105 ml (96 g) of catalyst consisting of 20.0% by weight of NiO, 67.42% by weight of $SiO_2$, 3.7% by weight of $Al_2O_3$, 0.8% by weight of $Fe_2O_3$, 0.76% by weight of MgO, 1.92% by weight of CaO, 3.4% by weight of $Na_2O$ and 2.0% by weight of $K_2O$, and the catalyst was then activated at atmospheric pressure in the course of 48 hours in a stream of hydrogen (200 l/h) by increasing the temperature from 30° C. to 250° C. After the temperature had been decreased to 110° C., a mixture of 50 ml/h of adiponitrile, 130 ml/h of ammonia and 200 l/h of hydrogen was fed to the reactor at 180 bar. Under these conditions, 25% of the adiponitrile were converted. The reaction mixture consisted essentially of 75% by weight of ADS, 24% by weight of ACN and 0.5% by weight of HMD. By increasing the reaction temperature to 120° C., the conversion increased to 60%. The reaction mixture consisted essentially of 40% by weight of ADN, 53% by weight of ACN and 5% of HMD. The catalyst had a constant activity over 100 hours.

Example 4

A tube reactor having a length of 2 m and an internal diameter of 2.5 cm was filled with 750 ml (1534 g) of a catalyst consisting of 90% b.w. of CoO, 5% b.w. of $Mn_2O_3$, 3% b.w. of $P_2O_5$ and 2% b.w. of $Na_2O$, and the catalyst was then activated at atmospheric pressure in the course of 48 hours in a stream of hydrogen (500 l/h) by increasing the temperature from 30° to 280° C. After the temperature had been decreased to 55° C. (entrance), 70° C. (exit) resp., a mixture of 400 ml/h of adipodinitrile, 1900 ml/h of ammonia and 500 l/h of hydrogen was fed to the reactor at 200 bar. Under these conditions, 50% of adipodinitrile were converted. The reaction mixture consisted of essentially of 50% b.w. of ADN, 39% b.w. of ACN, and 11% b.w. of HMD (ACN-selectivity: 78%, ACN+HMD-selectivity: 100%). After 3,000 hours the catalyst still had the same selectivity as fresh catalyst, the activity being unchanged.

Example 5

A catalyst was prepared according to Catalyst Manufacture, A. B. Stiles, T. A. Koch (1995) p. 167–168 by melting iron-oxide (magnetite) with the following promotors: $Al_2O_3$, $K_2O$ as $K_2CO_3$, and CaO as $CaCO_3$. Thereafter, the solidified melt was crushed. The obtained powder had the following composition: 1.1% b.w. $K_2O$, 3.0% b.w. $Al_2O_3$, 2.3% b.w. CaO, remainder $FeO/Fe_2O_3$.

After reduction of the above obtained oxidic powder at a temperature of 450° C. in a stream of hydrogen (without pressure) during ten hours, the thus treated powder was cooled down to room temperature in a stream of air and nitrogen. The thus obtained catalyst had a BET-surface of 6.5 m²/g and a carbon content of 0.055 %, based on the total amount of catalyst.

Three tube reactors in series (total length: 4.5 m, internal diameter 0.6 cm) were filled with 115 ml (303 g) of the above obtained catalyst, and the catalyst was then activated at atmospheric pressure in a stream of hydrogen (200 l/h) by increasing the temperature from 50° to 340° C. during the first 24 hours, and then kept at 340° C. during the following 72 hours. After the temperature had been decreased to 120° C., a mixture of 55 ml/h ADN, 260 ml/h ammonia and 200 l/h of hydrogen was fed to the reactor at 250 bar.

After a 200 hours the conversion of ADN was 47%. The reaction mixture consisted essentially of 53% b.w. ADN, 38% b.w. ACN and 8% b.w. HMD (ACN-selectivity: 80.9%, ACN+HMD-selectivity: 98%) during the following 400 hours.

Example 6

To an aqueous solution of cobalt nitrate, copper nitrate, manganese nitrate and phosphoric acid, consisting of 9.3% b.w. of cobalt, 2.7% b.w. of copper, 0.9% b.w. of manganese and 0.5% b.w. of phosphoric acid, based on the total amount of the solution, a 20% b.w. solution of sodium carbonate was added at a temperature of 50° C., yielding thereby a precipitate. The thus obtained precipitate was washed, until the wash water was free of sodium and nitrate. The washed precipitate was mixed with water and sprayed at a temperature of 550° C. (temperature at the entrance of a spraying tower). The sprayed powder was dried at 500° C., and processed to extrudates with a diameter of 4 mm. The extrudates were dried at a temperature in the range of 100° to 120° C. and then calcined at 900° C. for 1 h. Then, the calcined extrudates (66% b.w. CoO, 20% b.w. CuO, 7.3% b.w. $Mn_3O_4$, 3.6% b.w. $MoO_3$, 0.1% b.w. $Na_2O$, 3% b.w. $H_3PO_4$) were reduced in a stream of hydrogen at 320° C., and passivated in a stream of air and nitrogen at room temperature.

53 g of the above obtained passivated catalyst were reduced in a stream of hydrogen (20 l/h) at 200° C. for 10 hours and then filled into an autoclave with a volume of 270 ml. Then, 36 g ADN, 54 g (89 ml) ammonia were added. The following table shows the results of the hydrogenation:

TABLE ex. 6

| temp./ press. [°C./bar] | reaction time [h] | ACN- yield [%] | HMD- yield [%] | ACN- selectivity [%] | ADN-conversion [%] |
|---|---|---|---|---|---|
| 50/200 | 5 | 40 | 13 | 76 | 53 |
| 50/200 | 6 | 44 | 17 | 72 | 61 |

Example 7

142 g alpha-$Al_2O_3$ (Spheralite®512B, Rhône-Poulenc, spheres with a diameter in the range of 3 to 6 mm, water absorption=0.488 ml/g, bulk density=800 g/l) was impregnated with 69 ml of a solution of ruthenium nitrate, obtained by diluting 7.21 g of a solution of ruthenium nitrate with a Ru-content of 19.9% b.w. with water to a volume of 69 ml, for 30 minutes. Then the impregnated spheres were dried for 16 h at 120° C. and thereafter calcined for 4 h at 300° C., yielding a catalyst with 1% b.w. of Ru, based on the total amount of the catalyst.

Example 8

225 g $Al_2O_3$ (D10-12, from BASF, extrudates with a diameter of 4 mm, water absorption=0.44 ml/g, bulk density=879 g/l, BET-surface=95 m²/g) was impregnated with 100 ml of a solution of ruthenium nitrate, obtained by diluting 59.51 g of a solution of ruthenium nitrate with a Ru-content of 19.9% b.w. with water to a volume of 100 ml, for 120 minutes. Then the impregnated extrudates were dried for 16 h at 120° C. and thereafter calcined for 4 h at 300° C., yielding a catalyst with 5% b.w. Ru, based on the total amount of the catalyst.

Example 9

90 g Kieselguhr (extrudates with a diameter of 4 mm, water absorption=0.77 ml/g bulk density=504 g/l) was impregnated with 70 ml of a solution of ruthenium nitrate, obtained by diluting 4.57 g of a solution of ruthenium nitrate with a Ru-content of 19.9% b.w. with water to a volume of 70 ml, for 120 minutes. Then the impregnated extrudates were dried for 16 h at 120° C. and thereafter calcined for 4 h at 300° C., yielding a catalyst with 1% b.w. of Ru, based on the total amount of the catalyst.

Examples 10–12

31 ml catalyst were reduced in a stream of hydrogen (20 l/h) at 200° C. for 10 hours and then filled into an autoclave having a volume of 270 ml. Then, 36 g ADN and 54 g (89 ml) ammonia were added. The following table shows the results.

TABLE ex. 10-12

| ex. | temp./ press. [°C./bar] | reaction time [h] (ADN- conv. = 50%) | selectivity of ACN (ADN- conv. = 50%) | selectivity of ACN + HMD (ADN-conv. = 50%) |
|---|---|---|---|---|
| 7 | 130/200 | 2.9 | 72.4 | 99.3 |
| 8 | 50/200 | 1.7 | 80.4 | 99.1 |
| 9 | 110/200 | 4.3 | 75.1 | 99.2 |

Example 13

The catalyst of example 5 was washed with water for 24 hours at 60° C., yielding a catalyst with the following composition: 0.08% b.w. $K_2O$, 3.0% b.w. $Al_2O_3$, 2.3% b.w. CaO, remainder $FeO/Fe_2O_3$.

After reduction of the above obtained oxidic powder at a temperature of 450° C. in a stream of hydrogen (without pressure) during ten hours, the thus treated powder was cooled down to room temperature in a stream of air and nitrogen. The thus obtained catalyst had a BET-surface of 7 m²/g and a carbon content of 0.05%, based on the total amount of catalyst.

Three tube reactors in series (total length: 4.5 m, internal diameter 0.6 cm) were filled with 115 ml (290 g) of the above obtained catalyst, and the catalyst was then activated at atmospheric pressure in a stream of hydrogen (200 l/h) by increasing the temperature from 50° to 340° C. during the first 24 hours, and then kept at 340° C. during the following 72 hours. After the temperature had been decreased to 115° C., a mixture of 55 ml/h ADN, 260 ml/h ammonia and 200 l/h of hydrogen was fed to the reactor at 250 bar.

After 50 hours the conversion of ADN was 50%. The reaction mixture consisted essentially of 50% b.w. ADN, 42% b.w. ACN and 7.5% b.w. HMD (ACN-selectivity: 84%, ACN+HMD-selectivity: 99%) during the following 100 hours.

Example 14

To an aqueous solution of FeCl$_2$a solution of NaOH was added yielding a precipitate of γ-FeOOH, which was subsequently separated by filtration and dried at 120° C. for 16 hours. The dried powder was reduced at 400° C. in a fixed-bed with hydrogen without pressure to metallic iron powder. The thus obtained pyrophoric iron powder was passivated in a nitrogen/air mixture at 40° C. for 8 hours, welding a powder with a metallic iron content 93%. The thus passivated iron powder was mixed with 2% b.w. of graphite, based on the total amount of graphite and iron powder, and shaped into pellets (5 mm length, 3 mm diameter). The thus obtained catalyst had a BET-surface of 9 m$^2$/g.

31 ml (71 g) catalyst were reduced in a stream of hydrogen (10 l/h, without pressure) at 450° C. for 24 hours and then filled into an autoclave having a volume of 270 ml. Then, 36 g ADN and 54 g (89 ml) ammonia were added. The following table shows the results after 5 and 6.5 hours.

TABLE ex. 14

| temp./ press. [°C./bar] | reaction time [h] | yield (ACN) [%] | yield (HMD) [%] | ACN-select. [%] | conversion (ADN) [%] |
| --- | --- | --- | --- | --- | --- |
| 70/200 | 5 | 42.5 | 9 | 82 | 52 |
| 70/200 | 6.5 | 52 | 12 | 80 | 65 |

We claim:

1. In a process for the preparation of aliphatic alpha, omega-aminonitriles by partial hydrogenation of aliphatic alpha,omega-dinitriles at elevated temperature and superatmospheric pressure in the presence of a solvent and of a catalyst, the improvement which comprises hydrogenating an aliphatic alpha,omega dinitrile in the presence of a catalyst which (a) has a compound containing a metal selected from the group consisting of iron, nickel, ruthenium and rhodium and (b) has from 0.01 to 25% by weight, based on (a), of a promoter containing a metal selected from the group consisting of palladium, platinum, iridium, osmium, iron, copper, silver, gold, chromium, molybdenum, tungsten, manganese, rhenium, bismuth and rare earth metals, and (c) from 0 to 5% by weight, based on (a), of a trace component containing a metal selected from the group consisting of an alkali metal and an alkaline earth metal, with the proviso that the component (a) does not have iron or iron and one of the metals selected from the group consisting of cobalt, ruthenium and rhodium when (b) is a promoter having a metal selected from the group consisting of titanium, manganese, chromium and molybdenum, and with the further proviso that, when a compound based on only
  ruthenium or
  ruthenium and rhodium or
  rhodium and nickel is selected as component (a), the promoter (b) may, optionally, be dispensed with, whereby the catalyst is obtained by (I) precipitating precursors of the components (a) to (c) from aqueous solutions in the presence or absence of carriers yielding a precipitate, then (II) optionally processing the resulting precipitate to give extrudates or pellets, then (III) drying the precipitate or pellets or extrudates at a temperature of from 80° to 150° C. yielding a dried product, and (IV) then calcinating the dried product at a temperature from 150° to 1000° C. in a gas stream comprising air or nitrogen yielding a calcined product then (V) optionally, passivating the surface of the calcined product at from 20° to 80° C. by means of an oxygen/nitrogen mixture yielding a passivated product, then (VI) activating the calcined or passivated product by exposing it to a reducing atmosphere for from 2 to 24 hours at from 200° to 500° C.

* * * * *